United States Patent [19]

Morgan et al.

[11] 4,134,877
[45] Jan. 16, 1979

[54] FLAME RETARDANT PHOSPHORAMIDATE COMPOSITIONS

[75] Inventors: Albert W. Morgan, Collinsville, Ill.; Ignatius Schumacher; William Vanderlinde, both of St. Louis, Mo.

[73] Assignee: Monsanto Company, St. Louis, Mo.

[21] Appl. No.: 794,906

[22] Filed: May 9, 1977

Related U.S. Application Data

[60] Continuation-in-part of Ser. No. 599,568, Jul. 28, 1975, abandoned, which is a division of Ser. No. 459,257, Apr. 8, 1974, Pat. No. 4,062,909, which is a continuation-in-part of Ser. No. 276,810, Jul. 31, 1972, abandoned.

[51] Int. Cl.$^2$ .............................................. C08K 5/16
[52] U.S. Cl. ....................... 260/45.9 NP; 106/15 FP; 260/45.8 N; 260/45.8 NZ; 260/814
[58] Field of Search ........................ 260/45.9 NP, 814; 106/15 FP

[56] References Cited

U.S. PATENT DOCUMENTS 3,584,085  6/1971  Hartmann ..................... 260/45.9 NP
3,877,952  4/1975  Dahmen et al. ................. 106/15 FP

*Primary Examiner*—V. P. Hoke
*Attorney, Agent, or Firm*—George R. Beck; Robert E. Wexler; Edward P. Grattan

[57] ABSTRACT

Compounds of the formula

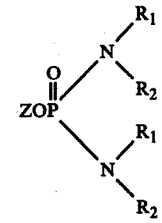

wherein:

Z represents a radical selected from the group consisting of alkyl or aryl radicals;

$R_1$ and $R_2$ may be the same or different and individually represent a radical selected from the group consisting of alkyl, cycloalkyl or aryl radicals; and $R_1$ and $R_2$ together with their common nitrogen atom represent a heterocyclic ring, impart flame retardant properties to natural and synthetic polymers.

15 Claims, No Drawings

FLAME RETARDANT PHOSPHORAMIDATE COMPOSITIONS

CROSS REFERENCES TO RELATED APPLICATIONS

This application is a continuation-in-part of U.S. Ser. No. 599,568, filed July 28, 1975, now abandoned which is a division of U.S. Ser. No. 459,257, filed Apr. 8, 1974, now U.S. Pat. No. 4,062,909 which, in turn, is a continuation-in-part of U.S. Ser. No. 276,810, filed July 31, 1972 and now abandoned.

PRIOR ART

The following patents, considered pertinent to the present invention, disclose phosphoroamidates prepared from simple aliphatic and aromatic alcohols, phosphorus oxyhalide and an amine: U.S. Pat. No. 2,385,713; U.S. Pat. No. 2,912,451; U.S. Pat. No. 3,531,550; and U.S. Pat. No. 3,584,085.

U.S. Pat. No. 2,385,713 discloses compounds of the formula $(Phenyl-O)_{\overline{m}}P(O)(NX_2)_n$ wherein $X = H$ or hydrocarbon and $m + n = 3$. The compounds are esters of amidophosphoric acids with substituted phenols and have utility as germicides and bactericides. With regard to the present invention, the patent indicates no distinction between the use of primary and secondary amines, contains an enabling disclosure directed only to "diamidophosphates" and, while disclosing compounds within the scope of this invention, does not teach the use of phosphorodiamidates as flame retardants.

U.S. Pat. No. 2,912,451 discloses acyclic tetramethylphosphorodiamidates having utility as weed killers. With regard to the present invention, the patent discloses amidation only with dimethylamine, makes only tetramethylphosphoroamidates and does not teach the use of phosphorodiamidates as flame retardants, although disclosing compounds falling within the scope of this invention.

U.S. Pat. No. 3,531,550 discloses certain phosphorus ester mono- and diamides having utility as functional fluids. With regard to the present invention, the patent does not teach the use of phosphorodiamidates as flame retardants, although disclosing compounds within the scope of this invention.

U.S. Pat. No. 3,584,085 discloses the use of certain phosphoromonoamides as flame retardants for polyurethanes. The patent prepares amides and hydroxyalkyl, halophenyl and alkyl-substituted amides which are not within the scope of this invention.

SUMMARY OF THE INVENTION

It has been found that phosphorodiamidates of the formula

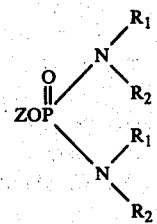

wherein:

Z represents a radical selected from the group consisting of alkyl or aryl radicals;

$R_1$ and $R_2$ may be the same or different and individually represent a radical selected from the group consisting of alkyl, cycloalkyl or aryl radicals; and $R_1$ and $R_2$ together with their common nitrogen atom represent a heterocyclic ring, impart flame retarding properties to natural and synthetic polymers.

DESCRIPTION OF THE PREFERRED EMBODIMENT

The compounds of this invention are prepared by reaction of a hydroxyl-containing moiety with a phosphorus oxyhalide to afford a phosphorohalidate which is then reacted with a secondary amine in an organic diluent containing an aqueous solution of an alkali metal hydroxide.

The compounds of this invention are represented by the formula

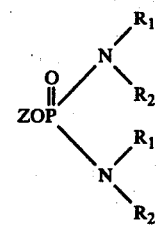

wherein:

Z represents a radical selected from the group consisting of alkyl or aryl radicals;

$R_1$ and $R_2$ may be the same or different and individually represent a radical selected from the group consisting of alkyl, cycloalkyl or aryl radicals; and $R_1$ and $R_2$ together with their common nitrogen atom represent a heterocyclic ring.

A generalized reaction scheme for preparing the compounds used in the invention is as follows:

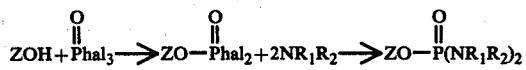

wherein Z, $R_1$ and $R_2$ are identified above.

Alcohols which are reacted with a phosphorus oxyhalide to obtain phosphorohalidates are represented by the formula ZOH, wherein Z is described above.

Exemplary aliphatic alcohols which are used include methanol, ethanol, propanol, isopropanol, butanol, isobutanol, nonanol, isononanol, decanol and octadecanol.

Aromatic alcohols include naphthol, benzyl alcohol, α-phenylethanol, β-phenoxyethanol, phenylallyl alcohol and diphenylcarbinol, vanillin and the phenols, e.g., phenol, allylphenol, cresol and ethylphenol.

Primary or secondary monohydroxy alcohols or phenols are the preferred hydroyl-containing material. Tertiary alcohols are unsuitable since reaction thereof with a phosphoryl halide affords an alkyl halide rather than a phosphorohalidate.

A preferred class of alcohols are represented by phenol, o, m, p-cresol, o-ethylphenol, o, m, p-isopropylphenol, p-tert-butylphenol, p-tert-amylphenol, nonylphenol, xylenol, o, m, p-chlorophenol, p-bromophenol, p-iodophenol, dichlorophenol, trichlorophenol, pentachlorophenol, p-cumylphenol, naphthol, methoxyphenol, ethoxyphenol, phenoxyphenol, p-nitrophenol, trifluoromethylphenol, allylphenol, benzylphenol, vanillin, 4-chloro-3,5-dimethylphenol, 4-chloro-1-naphthol, 2-chloro-4-nitrophenol, cyanophenol, di-tert-butylphenol, dimethoxyphenol, fluorophenol. Especially preferred of this group are phenol, cresol, cumylphenol, nonlyphenol, chlorophenol, xylenol, tert-butylphenol, phenylphenol and isopropyphenol.

It is essential that the alcohol contain no free-hydroxyl groups after the reaction with phosphorus oxyhalide since a free-hydroxyl group would react with any remaining P-chlorine linkages, thus leaving no reactive site for the subsequent amidation.

Alkyl radicals represented by $R_1$ and $R_2$ include methyl, ethyl, propyl, isopropyl, butyl, amyl, hexyl, heptyl, octyl, nonyl, decyl, and octadecyl.

Cycloalkyl radicals represented by $R_1$ and $R_2$ include cyclobutyl, cyclopentyl and cyclohexyl.

Aryl radicals represented by $R_1$ and $R_2$ include benzyl, β-phenylthyl, henyl and substituted phenyl, e.g., methyl phenyl, diethyl phenyl, naphthyl, chlorophenyl.

Heterocyclic rings formed by $R_1$ and $R_2$, together with their common nitrogen atom, are five-membered and six-membered rings wherein the nitrogen atom is associated with a reactive hydrogen atom. Thus, pyridine is unsuitable but hexahydropyridine is suitable. Suitable five- and six-membered rings include the pyrroles, e.g., pyrrole, dimethylpyrrole, pyrroline and pyrrolidine, the oxazoles such as oxazole and isooxazole, the pyrazoles such as pyrazole, pyrozoline and imidazole and six-membered rings such as hexahydropyridine (i.e., piperidine), the oxazines such as morpholine and diazines such as 1,3-diazine.

The phosphorus halides which are utilized herein include, for example, phosphorus oxytrichloride, phosphorus oxytribromide, phosphorus oxytrifluoride, phosphorus oxydichloride bromide, phosphorus oxydibromide chloride and phosphorus oxytrifluoride chloride.

The phosphorohalidates, which are reacted with a secondary amine to obtain the compounds useful in this invention, are prepared as described above and by methods known in the art. They are represented by the formula

wherein hal represents halogen, e.g., chlorine, fluorine, bromine or iodine and Z is defined above.

Illustrative phosphorohalidates utilized to prepare the novel compounds of this invention include phenyl phosphorodichloridate, chorophenyl phosphorodichloridate, chlorophenyl phosphorodibromidate, nitrophenyl phosphorodichloridate, cresyl phosphorodichloridate, methoxyphenyl phosphorodibromidate, nonylphenyl phosphorodichloridate, cumylphenyl phosphorodichloridate, biphenyl phosphorodichloridate, naphthyl phosphorodichoridate, isopropylphenyl phosphorodichloridate, tert-butylphenyl phosphorodichloridate and isodecylphenyl phosphorodichloridate.

The secondary amines utilized in accordance with this invention are characterized by the formula

wherein $R_1$ and $R_2$ are defined above. Preferably, one of $R_1$ and $R_2$ is methyl group.

Illustrative amines include the alkylamines, e.g., dimethylamine, methyl ethyl amine, methyl butyl amine, dibutyl amine, dioctyl amine, di-n-hexylamine, didecyl amine, di-n-octadecylamine; the arylamines, e.g., diphenylamine, dibenzylamine, di-(β-phenylethylamine), amines, e.g., di(butylcyclohexyl)amine, di(dicyclopentyl)amine; mixed alkyl-aryl amines, e.g., N-methylaniline and N-methyl toluidine, heterocyclic aines, e.g., piperidine, imidazole and morpholine.

The proportion of phosphorodihalidate and amine which are reacted will vary, depending upon reaction conditions. Generally, however, sufficient amine is added to completely convert the phosphorodihalidate to the corresponding phosphorodiamidate, e.g., two moles of more of amine per mole of phosphorodihalidate.

The reaction of the phosphorodihalidate and amine may be conducted in an aqueous medium but is preferably conducted in an organic diluent containing an aqueous solution of an alkali metal or ammonium hydroxide so that the alkali metal hydroxide will scavenge liberated hydrogen chloride. Organic diluents which may be used include any of the conventional organic diluents such as chlorobenzene, tetrahydrofuran and the like.

The temperature of the phosphorohalidate/amine reaction may vary from about 0° to about 100° C., although the preferred temperature range is from about 10° to about 60° C. Higher temperatures may be used but reduce yield.

The following examples illustrate specific embodiments of the invention are are not to be construed as limiting the scope thereof.

EXAMPLE I

In a one liter flask, fitted with reflux condenser thermometer and mechanical stirrer, are placed cumylphenol (424 gms.), phosphorus oxychloride (460 gms.) and pyridine (3.0 gms.). The mixture is heated to reflux which starts at 95° C. with evolution of hydrogen chloride. Over a period of three hours the temperature slowly rises to 145° C. and is maintained at that temperature for an additional one-half hour. The mixture is vacuum stripped to recover phosphorus oxychloride. The residue is diluted with monochlorobenzene (200 ml.) and added to a previously prepared solution of dimethylamine (800 gms. - 25 percent in water) and sodium hydroxide (350 gms. - 50 percent in water). The mixture is cooled to 15-20° C. during the addition over one and one-half hours. The mixture is then heated to 70° C. and the layers are separated. The organic layer is washed with water at 70° C., dehydrated, steamed and filtered.

The product (628 gms. - 91 percent yield) is cumylphenyl tetramethylphosphorodiamidate:

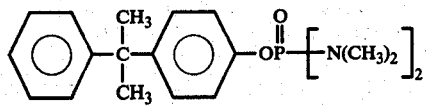

In the same fashion cumylphenol may be replaced by ethanol, butanol or octadecanol to afford, respectively, ethyl tetramethylphosphorodiamidate, butyl tetramethylphosphorodiamidate and octadecylphosphorodiamidate. Similarly, dimethylamine may be replaced by dibutylamine, dibenzylamine, diphenylamine or di(cyclohexylamine) to afford, respectively, cumylphenyl tetrabutylphosphorodiamidate, cumylphenyl tetrabenzylphosphorodiamidate, cumylphenyl tetraphenylphosphorodiamidate and cumylphenyl tetracyclohexylphosphorodiamidate.

EXAMPLE II

In a one liter flask, fitted with reflux condenser, mechanical stirrer and thermometer, are placed nonylphenol (440 gms.), phosphorus oxychloride (460 gms.) and pyridine (3.0 gms.). The procedure of Example I is then followed and the mixture residue is diluted with monochlorobenzene (200 ml.) and added to a morpholine (400 gms.)/caustic (350 gms.) solution. A ninety percent yield (787 gms.) of nonylphenyl dimorpholinophosphorodiamidate is obtained:

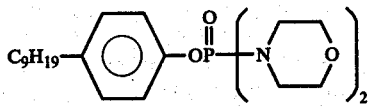

Repeating the above procedure with substitution of 800 gms. dimethylamine of 25 percent solution for 400 gms. morpholine affords a ninety percent yield (633 gms.) of nonylphenyl tetramethylphosphorodiamidate:

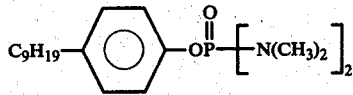

In the same fashion, morpholine may be replaced by piperidine and imidazole to afford, respectively, nonylphenyl dipiperidylphosphorodiamidate and nonyphenyl dimidazolylphosphorodiamidate. Similarly, nonylphenol may be replaced by β-phenylethanol, cyclopentanol, cresol or ethoxyphenol to afford, respectively, β-phenylethyl dimorpholinophosphorodiamidate, cyclopentyl dimorpholinophosphorodiamidate, cresyl dimorpholinophosphorodiamidate and ethoxyphenyl dimorpholinophosphorodiamidate. Additional compounds which may be prepared by replacing morpholine with a pyrrole, e.g., pyrrole, pyrroline, an oxazole, e.g., oxazole, or a diazine, e.g., 1,3-diazine, are nonylphenyl dipyrrolylphosphorodiamidate, ethyl dipyrrolinylphosphorodiamidate, cyclopentyl dioxazolylphosphorodiamidate and cresyl di-1,3-diaznylphosphorodiamidate.

The compounds of the present invention are useful as flame retardants for a wide variety of natural and synthetic polymer materials. The compounds are effective in concentrations of from about 0.1 percent by weight of polymer up to about 50 weight percent or more depending on the particular use for which the polymer material is intended.

Synthetic polymer materials, i.e., those high molecular weight organic materials which are not found in nature, with which the compounds of the invention are advantageously employed may be either linear or crosslinked polymers and may be in the form of sheets, coatings, foams and the like. They may be either those which are produced by addition or condensation polymerization An important class of polymers which are beneficially flame retarded with the compounds of the invention are those obtained from a polymerizable monomer compound having ethylenic unsaturation. A particularly preferred class of polymers which are flame retarded consist of the polymerized vinyl and vinylidene compounds. Such polymers are, for example, the solid polymeric alkenes, such as polyethylene, polypropylene, polyiosbutylene or ethylene/propylene copolymers; polymerized acrylyl and alkacrylyl compounds such as acrylic, fluoroacrylic and methacrylic acids, anhydrides, esters, nitriles and amides, for example, acrylonitrile, ethyl or butyl acrylate, methyl or ethyl methacrylate, methoxymethyl or 2-(2-butoxyethoxy)ethyl methacrylate, 2-(cyanoethoxy)ethyl 3-(3-cyanopropoxy)propyl acrylate or methacrylate, 2(diethylamino)ethyl or 2-chloroethyl acrylate or methacrylate, acrylic anhydride or methacrylic anhydride; methacrylamide or chloroacrylamide; ethyl or butyl chloroacrylate; the olefinic aldehydes such as acrolein, methacrolein and their acetals; the vinyl and vinylidene halides such as vinyl chloride, vinyl fluoride, vinylidene fluoride and 1-chloro-1-fluoroethylene; polyvinyl alcohol; the vinyl carboxylates such as vinyl acetate, vinyl chloroacetate, vinyl propionate, and vinyl 2-ethyl-hexanoate; the N-vinyl imides such as N-vinyl phthalimide and N-vinyl-succinimide; the N-vinyl lactams such as N-vinyl caprolactam and N-vinyl butyrolactam; vinyl aromatic hydrocarbon compounds such as styrene, alpha-methylstyrene, 2,4-dichlorostyrene, alpha- or beta-vinylnaphthalene, divinyl benzene and vinyl fluorene; the vinyl ethers such as ethyl vinyl ether or isobutyl vinyl ether; vinylsubstituted heterocyclic compounds such as vinyl pyridine, vinyl pyrrolidone, vinylfuran or vinylthiophene; the vinyl or vinylidene ketones such as methyl vinyl ketone or isopropenyl ethyl ketone; vinylidene cyanide. Homopolymers of the above compounds or copolymers and terpolymers thereof are beneficially flame retarded by the compounds of the present invention. Examples of such copolymers or terpolymers are those obtained by polymerization of the following monomer mixtures: vinyl chloride/vinyl acetate, ethylene/vinyl chloride/vinyl acetate, acrylonitrile/vinyl pyridine, styrene/methyl methacrylate, styrene/N-vinyl pyrrolidone, cyclohexyl methacrylate/vinyl chloroacetate, acrylonitrile/vinylidene cyanide, methyl methacrylate/vinyl acetate, ethyl acrylate/methacrylamide/ethyl chloroacrylate, vinyl chloride/vinylidene chloride/vinyl acetate.

Other polymers of compounds having the ethylenic group are homopolymers, copolymers and terpolymers of the alpha-, beta-olefinic dicarboxylic acids and derivatives thereof such as the anhydrides, esters, amides, nitriles and imides, for example, methyl, butyl, 2-ethylhexyl or dodecyl fumarate or maleate; maleic chloromaleic, citraconic or itaconic anhydride; fumaronitrile, dichlorofumaronitrile or citracononitrile; fumaramide, maleamide or N-phenyl maleamide. Examples of particulary useful polymers and terpolymers prepared from the alpha-, beta-olefinic dicarboxylic compounds are the copolymers of maleic anhydride and a vinyl compound such as ethylene, propylene, isobutylene, styrene, alpha methylstyrene, vinyl acetate, vinyl propionate, methyl isopropenyl ketone, isobutyl vinyl ether, the copolymers of dialkyl fumarate such as ethyl or butyl fumarate and vinyl compounds such as styrene, vinyl acetate, vinylidene chloride, ethyl methyacrylate, acrylonitrile and the like.

The compounds of the invention act as flame retardants for the polymers and copolymers of unsaturated, cyclic esters of carbonic acid, for example, homopolymeric vinylene carbonate or the copolymers of vinylene carbonte with ethylenic compounds such as ethylene, vinyl choride, vinyl acetate, 1,3-butadiene, acrylonitrile, methacrylonitrile, or the esters of methacrylic or acrylic acid.

Readily flame retarded by the compounds of the invention are also the polyarylcarbonate polyners such as the linear polyarylcarbonates formed from diphenols or dihydroxy aromatic compounds including single and fused-ring nuclei with two hydroxy groups as well as monohydroxy-substituted aromatic residues joined in paris by various connecting linkages. Examples of the foregoing include dihydroxy benzenes, naphthalenes and the like, the dihydroxydiphenyl ethers, sulfones, alkanes, ketones and the like.

The compounds of the invention also act as flame retardants for polymers, copolymers or terpolymers of polymerizable compounds having a plurality of double bonds, for example, rubbery, conjugated diene polymerizates such as homopolymerized 3-butadiene, 2-chlorobutadiene or isoprene and linear copolymers or terpolymers such as butadiene/acrylonitrile, isobutylene/butadiene, butadiene/styrene; esters of saturated di- or poly-hydroxy compounds with olefinic carboxylic acids such as ethylene glycol dimethacrylate, triethylene glycol dicrotonate or glyceryl triacrylate; esters of olefinic alcohols with dicarboxylic acids or with olefinic monocarboxylic acids such as diallyl adipate, divinyl succinate, diallyl fumarate, allyl methacrylate or crotyl acrylate and other diethylenically unsaturated compounds such as diallyl carbonate, divinyl ether of divinylbenzene, as well as the crosslinked polymeric materials such as methyl methacrylate/diallyl methacrylate copolymer or butadiene/styrene/divinyl benzene terpolymer.

The cellulose derivaties are flame retarded by the compounds of the present invention. For example, cellulose esters such as cellulose acetate, cellulose triacetate or cellulose butyrate, the cellulose ethers such as methyl or ethyl cellulose, cellulose nitrate, carboxymethyl cellulose, cellophane, rayon, regenerated rayon and the like may be flame retarded.

The compounds of the present invention are well suited for flame retarding liquid resin compositions of the polyester type, for example, the linear polyesters which are obtained by the reaction of one or more polyhydric alcohols with one or more alpha-, beta- unsaturated polycarboxylic acids alone or in combination with one or more saturated polycarboxylic acid compounds, or the crosslinked polyester resins which are obtained by reacting a linear polyester with a compound containing a vinyl group.

The compounds of the present invention are compatible flame retardants for epoxy resins. Such resins are condensation products formed by the reaction of a polyhydroxy compound and epichlorohydrin, which condensation products are subsequently cured by the addition of crosslinking agents. The hydroxy compounds may be, for example, ethylene glycol, 4,4-isopropylidenediphenol and similar materials. The crosslinking agent employed in the curing step may be a dicarboxylic compound such as phthalic anhydride or adipic acid, but is more generally a polyamine such as ethylene diamine, paraphenylamine diamine or diethylene triamine.

Polyurethanes are a class of polymer materials which are flame retarded by the compounds of the present invention. The polyrurethanes, like the above-mentioned polyesters, are materials which are employed in structural applications, for example, as insulating foams, in the manufacture of textile fibers, as resin bases in the manufacture in curable coating compositions and as impregnating adhesives in the fabrication of laminates of wood and other fibrous materials. Especially, the polyurethanes are condensation products of a diisocyanate and a compound having molecular weight of at least 500 and preferably about 1500–5000 and at least two reative hydrogen ions. The useful active-hydrogen containing compounds may be polyesters prepared from polycarboxylic acids and polyhydric alcohols, polyhydric polyalkylene ethers having at least two hydroxy groups, polythioether glycols, polyesteramides and similar materials.

The polyesters or polyester amides used for the production of the polyurethane may be branched and/or linear, for example, the esters of adipic, sebasic, 6-aminocapoic, phthalic, isophthalic, terephthalic, oxalic, malonic, succinic, maleic, cyclohexane-1,2-dicarboxylic, cyclohexane-1,4-dicarboxylic, polyacrylic, naphthalene-1,2-dicarboxylic, fumaric or itaconic acids which polyalcohols such as ethylene glycol, diethylene glycol, pentaglycol, glycerol, sorbitol, triethanolamine and/or amino alcohols such as ethanolamine, 3-aminopropanol, and with mixtures of the above polyalcohols and amines.

The alkylene glycols and polyalkylene or polythioalkylene glycols used in the production of polyurethanes may be ethylene glycol, propylene glycol, butylene glycol, diethylene glycol, triethylene glycol, polythioethylene glycol, dipropylene glycol and the like.

Generally, any of the polyesters, polysiocyanate-modified polyesters, polyester amides, polyisocyanate-modified polyester-amides, alkylene glycols, polyisocyanate-modified alkylene glycols, polyoxyalkylene glycols and polyisocyanate-modified polyoxyalkylene glycols having three reactive hydrogen atoms, three reactive carboxylic and/or especially hydroxyl groups may be employed in the production of polyurethanes. Moreover, any organic compound containing at least two radicals selected fronm the group consisting of hydroxy and carboxy groups may be employed.

The organic polyisocyanates useful for the production of polyurethanes include ethylene diisocyanate, ethylidene diisocyanate, propylene-1,2-diisocyanate, m-phenylene diisocyanate, 2,4-tolyene diisocyanate, triphenylmethane triisocyanate, or polyisocyanates in blocked or inactive form such as the bisphenyl carbamates of tolyene diisocyanate and the like. Phenolic resins are flame retarded by the compounds of the present invention, which compounds may be incorporated into phenolc resin either by milling and molding applications or by addition to film-forming or impregnating and bonding solutions prior to casting. Phenolic resins with which the present compounds are employed are, for example, the phenolaldehyde resins prepared from phenols such as phenol, cresol, xylinol, resorcinol, 4-butylphenol, cumylphenol, 4-phenylphenol, nonylphenol, and aldehydes such as formaldehyde, actaldehyde or butyraldehyde in the presence of either acetic or basic catalysts, depending upon whether the resin is intended for use as a molding or extruding resin or as the resin base in coating and impregnating compositions.

Aminoplasts are another group of aldehyde resins which are flame retarded by the compounds of the invention. Examples of aminoplasts are the heat-convertible condensation products of an aldehyde with urea, thiourea, guanidine, cyanamide, dicyandiamide, alkyl or aryl guanamines and the triazines such as melamine, 2-fluoro-4,6-diamino-1,3,5-triazine and the like. When the aminoplasts are to be used as impregnating agents, bonding adhesives, coatings and in casting of films, the compounds of the present invention are incorporated into solutions or suspension in which the aminoplast is carried. The resulting mixtures give strong, fire-retardant laminates when sheets of paper, glass, cloth or fabric are impregnated therewith and cured.

Another class of compounds which are flame retarded by the compounds of the present invention are the nylons, for example, the superpolyamides which are generally obtained by the condensation of a diamine, for example, hexamethylene diamine with a dicarboxylic acid, for example, adipic acid.

Other polyamides which are flame retarded in accordance with the present invention are the polypeptides which may be prepared, for example, by reaction of N-carbobenzyl oxyglycine with glycine or mixture or glycine and lysine or an N-carboxy amino acid anhydrine such as N-carboxyl-DL-phenylalanine anhydride, piperidone, 2-oxohexamethyleneimine and other cyclic amides. The compounds of the present invention can be incorporated into molding or extruding compositions for a flame retardant effect.

The compounds of the present invention are also useful as flame retardants for linear polymers obtained by the self-condenstation of bifunctional compounds, for example, the polyethers which are derived by the self-condensation of dihydric alcohols such as ethylene glycol, propylene glycol or hexamethylene glycol; the polyesters which are obtained by the self-condensation of hydroxy acids such as lactic acid or 4-hydroxybutyric acid; the polyamides which are prepared by the self-condensation of aminocarboxylic acids such as 4-aminobutyric acid; the polyanhydrides which are formed by the self-condensation of dicarboxylic acids such as sebasic or adipic acid.

The preferred synthetic polymer materials which are flame retarded by the compounds of the present invention are the vinyl halide polymers in the form of milled products, plastisols and foams, rigid and flexible polyurethane coatings and foams, epoxy resins, ABS AND GRS rubbers, aminoplasts and phenolics. The vinyl halide polymers can be simple, mixed homopolymers of vinyl chloride or vinylidene chloride, such as polyvinyl chloride or polyvinylidene chloride, or copolymers or terpolymers in which the essential polymeric structure of polyvinyl chloride is interspersed at intervals with residues of other ethylenically unsaturated compounds copolymerizable therewith. The essential properties of the polymeric structure of polyvinyl chloride is retained if not more than about 40 percent of a comonomer is copolymerized therewith. Especially preferred copolymers include ethylene/vinyl chloride and vinyl chloride/acrylonitrile copolymers. Especially preferred terpolymers include ethylene/vinyl chloride/acrylonitrile, ethylene/vinyl chloride/acrylic acid and ethylene/vinyl chloride/acrylamide terpolymers.

Natural polymeric materials which may be flame retarded by the compounds of the present invention include natural rubber, cellulose esters, for example, cellulose acetate and cellulose nitrate, ethyl cellulose, cork and wood flour products and similar cellulosic materials.

The polymer formulations which are flame retarded in accordance with the present invention, whether in sheet or film form or of foam or molded structure, may contain various conventional additives such as fillers, extenders, crosslinking agents and colorants. Minor amounts of stabilizers, for example, are usually incoporated to reduce the effects of heat and light.

When foamable compositions are used, the composition may be a self-blowing polymer or the polymer may be blown by chemical or mechanical means or by the use of compressed gas. Fillers which are frequently employed to lower the cost of the finished material and to modify its properties include calcium carbonate and magnesium silicate. When fillers are employed, they are generally present in an amount of up to about 150 parts by weight of filler per 100 parts by weight of polyer formulation.

Where a colored or tinted composition is desired, colorants or color-pigments are incorporated in amounts of from about one to about five parts by weight to 100 parts by weight of polymer.

Surfactants such as silicones are normally added to foam formulations which are mechanically frothed. The surfactants reduce the surface tension of the foam and thereby increase the air or gas entrapment characteristics of the foam.

Additionally, glass-forming inorganic materials such as zinc borate, zinc oxide, lead oxide, lead silicate and silicon dioxide may be added to decrease the flame and smoke generating characteristics of the polymer. The flame retardant compounds of the present invention are extremely advantageous because of the following combination of properties: (1) The compounds are stable at temperatures somewhat in excess of 350° C. and can therefore be processed on standard machinery, such as milling machines, without degradation or color loss. (2) The compounds contain little or no chlorine and therefore contribute little or no hydrogen chloride gas during exposure to flames. (3) The compounds are amenable to formulation with a less stable acid generator and therefore can be made todegrade at lower temperatures if necessary. (4) The compounds are excellent acid scavengers, thereby decreasing the amount of acid radicals evolved by burning materials. (5) The compounds have high solubility and compatability with a wide variety of synthetic and natural polymer materials.

What is claimed is:

1. A composition comprising a polymer and an effective flame retarding amount of a compound of the formula

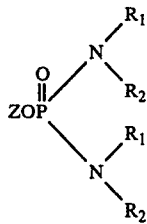

wherein

Z is selected from alkyl, benzyl, phenylethyl, naphthyl, phenyl, cresyl, ethylphenyl, isopropylphenyl, tert-butylphenyl, tert-amylphenyl, nonylphenyl, xylenyl, chlorophenyl, bromophenyl, iodophenyl, dichlorophenyl, trichlorophenyl, pentachlorophenyl, cumylphenyl, methoxyphenyl, ethoxyphenyl, phenoxyphenyl, nitrophenyl, trifluoromethylphenyl, benzylphenyl, vanillyl, chlorodimethylphenyl, chloronaphthyl, chloronitrophenyl, cyanophenyl, di-tert-butylphenyl, dimethoxyphenyl, fluorophenyl, biphenyl, and isodecylphenyl; and $R_1$ and $R_2$ are individually selected from alkyl, cycloalkyl, benzyl, phenylethyl, phenyl, methylphenyl, diethylphenyl naphthyl and chlorophenyl.

2. Composition of claim 1 wherein Z is selected from phenyl, cresyl, cumylphenyl, nonylphenyl, chlorophenyl, xylenyl, tert-butylphenyl, phenylphenyl and isopropylphenyl.

3. A composition of claim 1 wherein said polymer is selected from natural rubber and a natural cellulose ester.

4. Composition of claim 1 wherein said polymer is a synthetic polymer selected from the group consisting of vinyl polymers, polyurethanes, polyesters and vinyl halide polymers.

5. Composition of claim 1 wherein Z represents an alkyl radical.

6. Composition of claim 5 wherein $R_1$ and $R_2$ represent alkyl radicals.

7. Composition of claim 6 wherein $R_1$ and $R_2$ are methyl radicals.

8. Composition of claim 5 wherein $R_1$ and $R_2$ represent cycloalkyl radicals.

9. Composition of claim 8 wherein said cycloalkyl radicals are cyclohexyl radicals.

10. Composition of claim 5 wherein $R_1$ and $R_2$ represent phenyl radicals.

11. Composition of claim 2 wherein $R_1$ and $R_2$ represent alkyl radicals.

12. Composition of claim 11 wherein $R_1$ and $R_2$ are methyl radicals.

13. Composition of claim 2 wherein $R_1$ and $R_2$ represent cycloalkyl radicals.

14. Composition of claim 13 wherein said cycloalkyl radicals are cyclohexyl radicals.

15. Composition of claim 2 wherein $r_1$ and $R_2$ are phenyl radicals.

UNITED STATES PATENT AND TRADEMARK OFFICE
CERTIFICATE OF CORRECTION

PATENT NO. : 4,134,877

DATED : January 16, 1979

INVENTOR(S) : Albert W. Morgan, Ignatius Schumacher and William Vanderlinde

It is certified that error appears in the above-identified patent and that said Letters Patent are hereby corrected as shown below:

Column 2, line 54, omit "-" at end of line.

Column 3, line 9, "isopropyphenol" should read -- isopropylphenol --.

Column 3, line 22, "β-phenylthyl, henyl" should read -- β-phenylethyl, phenyl --.

Column 3, line 41, "oxytrifluoride" should read -- oxydifluoride --.

Column 4, line 9, insert "a" after "is".

Column 4, line 18, "aines" should read -- amines --.

Column 4, line 25, "of (first occurrence)" should read -- or --.

Column 5, line 62, "di-1,3-diaznylphos-" should read -- di-1,3-diazinylphos- --.

Column 7, line 49, "derivaties" should read -- derivatives --.

Column 8, line 4, "4,4-iso-" should read -- 4,4'-iso- --.

Column 8, line 23, "reative" should read -- reactive --.

Column 8, line 41, "polyalkylene" should read -- polyoxyalkylene --.

Column 9, line 36, "drine" should read -- dride --.

Column 9, line 36, "N-carboxyl-DL-phenylalanine" should read -- N-carboxy-DL-phenylalanine --.

UNITED STATES PATENT AND TRADEMARK OFFICE
CERTIFICATE OF CORRECTION

PATENT NO. : 4,134,877

DATED : January 16, 1979

INVENTOR(S) : Albert W. Morgan, Ignatius Schumacher and William Vanderlinde

It is certified that error appears in the above-identified patent and that said Letters Patent are hereby corrected as shown below:

Column 9, line 58, "AND (second occurrence)" should read -- and --

Column 10, line 31, "polyer" should read -- polymer --.

Column 10, line 63, "compatability" should read -- compatibility --

Column 11, line 26, insert "," after "thylphenyl".

Column 12, line 28, "$r_1$" should read -- $R_1$ --.

Signed and Sealed this

Thirteenth Day of November 1979

[SEAL]

Attest:

RUTH C. MASON
*Attesting Officer*

LUTRELLE F. PARKER
*Acting Commissioner of Patents and Trademarks*